(12) United States Patent
Schumaier

(10) Patent No.: US 9,730,837 B1
(45) Date of Patent: Aug. 15, 2017

(54) EARPLUG SOUND BLOCKER

(71) Applicant: Daniel R. Schumaier, Elizabethton, TN (US)

(72) Inventor: Daniel R. Schumaier, Elizabethton, TN (US)

( * ) Notice: Subject to any disclaimer, the term of this patent is extended or adjusted under 35 U.S.C. 154(b) by 0 days.

(21) Appl. No.: 15/190,645

(22) Filed: Jun. 23, 2016

(51) Int. Cl.
*A61F 11/08* (2006.01)
*A61F 11/06* (2006.01)

(52) U.S. Cl.
CPC ......... *A61F 11/08* (2013.01); *A61F 2011/085* (2013.01)

(58) Field of Classification Search
CPC ...... A61F 11/08; A61F 11/12; A61F 2011/085
USPC ........ 181/135, 130, 136, 133; 381/328, 329, 381/324, 322; 128/867, 866
See application file for complete search history.

(56) References Cited

U.S. PATENT DOCUMENTS

| | | | |
|---|---|---|---|
| 1,893,143 A | | 1/1933 | Koch |
| 1,893,474 A | | 1/1933 | Lieber |
| 2,437,490 A | * | 3/1948 | Watson .................. A61F 11/08 128/867 |
| 2,477,046 A | | 7/1949 | Davenport |
| 2,785,675 A | * | 3/1957 | Berkman ............... A61F 11/08 128/867 |
| 3,041,856 A | | 7/1962 | Neal |
| 3,169,523 A | * | 2/1965 | French .................. A61F 11/08 128/864 |
| 3,415,246 A | * | 12/1968 | Hill ....................... A61F 11/08 128/864 |
| 4,582,053 A | * | 4/1986 | Wilson .................. A61F 11/08 128/867 |
| 4,702,238 A | * | 10/1987 | Scott ..................... A61F 11/08 128/867 |
| 4,803,853 A | | 2/1989 | Hoerkens |
| 5,488,961 A | * | 2/1996 | Adams ................... A61F 11/08 128/864 |
| 5,631,965 A | * | 5/1997 | Chang ................... A61F 11/08 381/72 |
| 5,881,729 A | * | 3/1999 | Castillo ................. A61F 11/08 128/864 |
| 5,957,136 A | * | 9/1999 | Magidson .............. A61F 11/08 128/864 |
| 6,148,821 A | | 11/2000 | Falco |

(Continued)

FOREIGN PATENT DOCUMENTS

| | | |
|---|---|---|
| EP | 0590698 A2 | 4/1994 |
| EP | 0478892 B1 | 10/1994 |

(Continued)

OTHER PUBLICATIONS

Alpine Hearing Protection, Alpine MusicSafe Pro, http://www.alpinehearingprotection.com/earplugs/musicsafe-pro/, Accessed Apr. 26, 2016.

(Continued)

*Primary Examiner* — Edgardo San Martin
(74) *Attorney, Agent, or Firm* — Luedeka Neely Group PC

(57) ABSTRACT

An earplug and earplug kit having an ear insert, one or more filters that are interchangeable and that may be removably mounted to the insert for filtering various levels and types of sounds, and one or more decorative sound blocking members that are interchangeable and that may be removably mounted to the insert for reflecting or absorbing at least a portion of sounds directed toward a user's ear.

21 Claims, 6 Drawing Sheets

(56) References Cited

U.S. PATENT DOCUMENTS

| | | | |
|---|---|---|---|
| 6,938,622 B2 | 9/2005 | Huang | |
| 7,221,769 B1 | 5/2007 | Jorgensen | |
| 8,054,985 B2* | 11/2011 | Doty | A61F 11/08 381/322 |
| 8,111,861 B2 | 2/2012 | Lowry | |
| 8,161,975 B2 | 4/2012 | Turdjian | |
| 8,931,489 B2* | 1/2015 | Smith | A61F 11/08 128/864 |
| 9,278,031 B2 | 3/2016 | Brown | |
| 9,294,831 B2 | 3/2016 | Tan et al. | |
| 9,333,116 B2* | 5/2016 | Bauman | A61F 11/08 |
| 9,398,364 B2* | 7/2016 | Monahan | H04R 1/1016 |
| 2003/0159878 A1* | 8/2003 | Hakansson | A61F 11/08 181/135 |
| 2003/0174853 A1 | 9/2003 | Howes et al. | |
| 2007/0116309 A1* | 5/2007 | Smith | H04R 1/1016 381/313 |
| 2007/0125590 A1 | 6/2007 | Oberdanner | |
| 2008/0025539 A1 | 1/2008 | Bailey et al. | |
| 2008/0276945 A1* | 11/2008 | Rosen | A61F 11/08 128/864 |
| 2014/0190494 A1* | 7/2014 | Ely | A61F 11/12 128/868 |
| 2014/0254852 A1 | 9/2014 | Haapapuro et al. | |
| 2014/0270257 A1 | 9/2014 | Bauman et al. | |
| 2016/0022498 A1 | 1/2016 | Dittrich et al. | |
| 2016/0045373 A1* | 2/2016 | Williams | A61F 11/12 181/135 |
| 2016/0206477 A1* | 7/2016 | Davidson | A61F 11/08 |

FOREIGN PATENT DOCUMENTS

| | | | |
|---|---|---|---|
| EP | 1629805 A1 | 3/2006 | |
| KR | WO 2015160196 A1 * | 10/2015 | A61F 11/08 |

OTHER PUBLICATIONS

Review: ProSounds X-Pro ear plugs turn on and off with a click; http://www.gizmag.com/review-prosounds-s-pro-ear-plugs/38617/; Accessed Apr. 25, 2016.

* cited by examiner

EARPLUG SOUND BLOCKER

FIELD

The present disclosure relates to earplugs. More particularly, the present invention relates to an earplug having an ear insert, a removable filter inserted into the insert, and an ornamental faceplate mounted to the filter for absorbing or reflecting sound waves directed toward a user's ear.

BACKGROUND & SUMMARY

In manufacturing, live musical performances, construction and other noisy environments, continued exposure to high sound levels can cause hearing loss. Repeated exposure to noise levels above 90 decibels can cause hearing loss in a relatively short time. Hearing loss has become such a problem in the United States that OSHA requires any workers who are continually exposed to an ambient noise level above 90 decibels to wear hearing protection. Hearing loss arising out of continued exposure to high sound levels can easily be avoided or greatly reduced by using hearing protection devices, such as earplugs.

There are many types of earplugs. Foam earplugs are a type of hearing protection used in noisy environments to protect against hearing loss. Foam earplugs can be fabricated from a variety of materials including silicon, various plastics, PVC, and polyethylene. Two of the more common materials used are PVC and polyethylene. These materials provide an earplug which can be compressed to a small diameter and inserted into the ear canal. Once in the ear canal, the earplug slowly expands or recovers to seal against the interior surface of the ear canal and inhibit noise or sound from entering the ear canal. Flanged earplugs are a second type of hearing protection that typically include a flexible body having one or more flanges extending away from the body that form a seal within the ear canal.

A common problem with earplugs is that they are not sufficiently customizable. Often, only a few designs of earplug are provided. In one aspect, the level of attenuation or sound reduction provided by an earplug is fixed. In many cases, it may be desirable to have hearing protection where the sound filtering characteristics, including the volume and type of sound filtered, be easily changeable. Additionally, while the appearance of the earplugs is typically static and not easily changed, it may be desirable in certain circumstances to change the appearance of the earplug.

What is needed, therefore, is an earplug that is highly customizable in both attenuation or filtering characteristics as well as in appearance.

The above and other needs are met by an earplug and earplug kit having an ear insert, one or more interchangeable filters that may be removably mounted to the insert for filtering various levels and types of sounds, and one or more interchangeable sound blocking members that may be removably mounted to the insert to reflect or absorb a portion of sounds directed toward a user's ear.

In a preferred embodiment, the ear insert has inner and outer portions, where the inner portion is sized and configured for insertion into an ear canal such that it will attenuate sound waves directed toward the ear canal. The ear insert includes a flexible body defining an elongate shape having an internal channel extending there through that is configured to permit sound waves to pass through the earplug and into the ear canal. The flexible body may include at least one conformable vane or flange that projects from an external surface of the flexible body and is configured to work cooperatively with the flexible body to conform to a portion of the ear canal when the inner portion of the ear plug is inserted into the ear.

The removable filter may be inserted into the internal channel of the ear insert. The filter has an insertion tip configured for insertion into the internal channel of the ear insert and a stop configured to abut the outer portion of the ear insert. In some embodiments, the stop is cylindrical in shape and has a first raised ridge located adjacent to the insertion tip that abuts the outer portion of the ear insert, a center portion, and a second raised ridge following the center portion of the cylindrical stop. The internal channel may have a first diameter at the inner portion and a second diameter at the outer portion, such that the sound blocking member removably engages only one end of the ear insert and not the opposite end.

The removable filter includes filter media for attenuating sound waves passing into the ear canal through the internal channel. An internal channel extends through the filter and is configured to permit filtered sound waves to pass through the filter. The filter media are disposed in the internal channels of the filters. In certain embodiments, the filter media may be removed from the filter and replaced with different filter media having alternate filtering characteristics.

The sound blocking member attaches to the outer portion of the ear insert and may reflect or absorb a portion of sound waves directed toward the ear canal. The sound blocking member may be flat and plate-like and polygonal in shape. Alternatively, the sound blocking member may be contoured or have projections, including ridges or lips that extend away from the front surface. In certain embodiments, the sound blocking member includes an opening configured to engage the stop. For example, the opening may slide over one raised ridge of the stop and then be retained in the unraised center by the ridges. In certain embodiments, the sound blocking member extends away from the stop and covers a portion of a concha of the ear.

The sound blocking member may also be decorative. An ornamental design may be located on the front or back surface or, instead, may be formed into the sound blocking member itself. In certain cases, especially where the ornamental design is applied to the back surface of the sound blocking member, the sound blocking member is at least partially transparent so the design is visible when looking at the front surface.

BRIEF DESCRIPTION OF THE DRAWINGS

Further advantages of the disclosure are apparent by reference to the detailed description when considered in conjunction with the figures, which are not to scale so as to more clearly show the details, wherein the reference numbers indicate like elements throughout the several views, and wherein.

DETAILED DESCRIPTION

Figure 1:
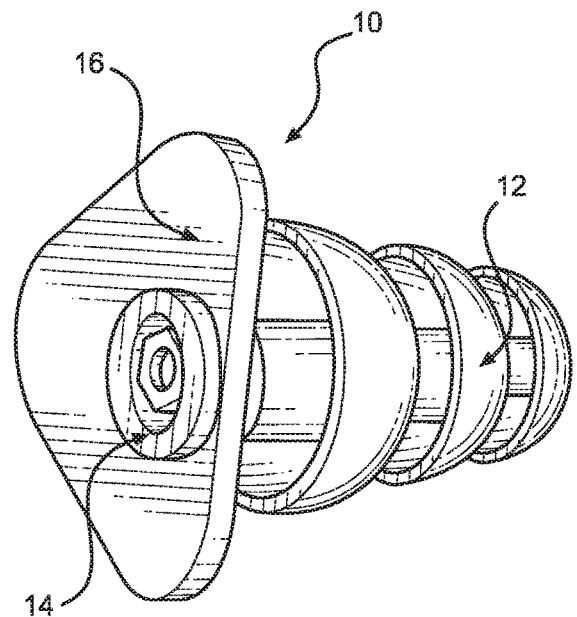
FIG. 1 is a depiction of a fully assembled earplug having a sound blocking member installed onto a filter and ear insert.

FIG. 1 depicts an earplug 10 comprising an ear insert 12, a filter 14 mounted to the ear insert, and a sound blocking member 16 mounted to the filter. The ear insert 12 attenuates sound waves directed toward the ear canal of the user. The filter 14 may be removed and replaced with a different filter having different filtering characteristics to attenuate different levels or types of sound. The sound blocking member 16 may absorb or reflect some of the sound waves directed toward the user's ear canal. Also, the sound blocking member 16 may have an ornamental design on its surface to improve the aesthetics of the earplug 10. The sound blocking member 16 may be removed and replaced with a sound blocking member having a different size of shape or one having a different ornamental design. The various aspects of embodiments of the invention discussed above are described in greater detail below.

Figure 2:
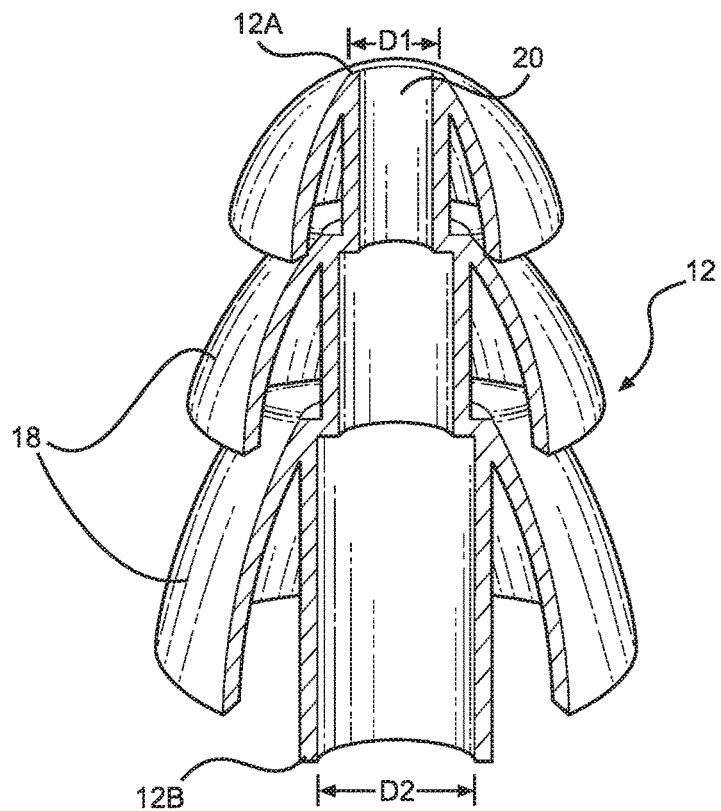
FIG. 2 is a front perspective view of an ear insert according to an embodiment of the present invention.
Figure 3:
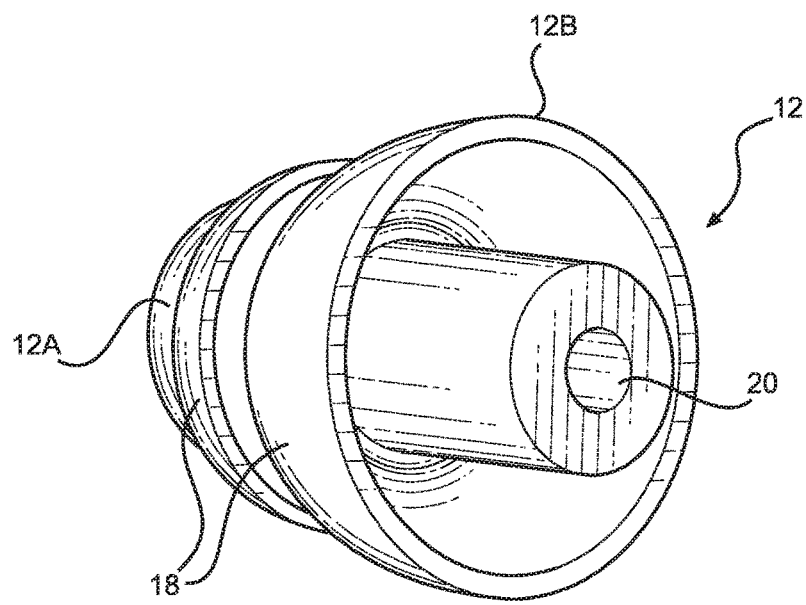
FIG. 3 is a perspective view illustrating an outer portion of the ear insert shown in FIG. 2.

With reference to FIGS. 2 and 3, one preferred embodiment of the ear insert 12 has a flexible body defining an elongate shape that includes both an inner portion 12A that is sized and configured for insertion into an ear canal of a user as well as an outer portion 12B. There is at least one conformable vane 18 projecting from an external surface of the flexible body configured to work cooperatively with the flexible body to conform to a portion of the ear canal when the inner portion 12A of the ear plug is inserted into the ear. Once the ear insert 12 has been inserted, sound waves travel into the ear canal via an internal channel 20 that extends from the outer portion 12B through the inner portion 12A. In other embodiments, a foam insert 12 may be used in place of the conformable vane-type of insert discussed above.

Figure 4:
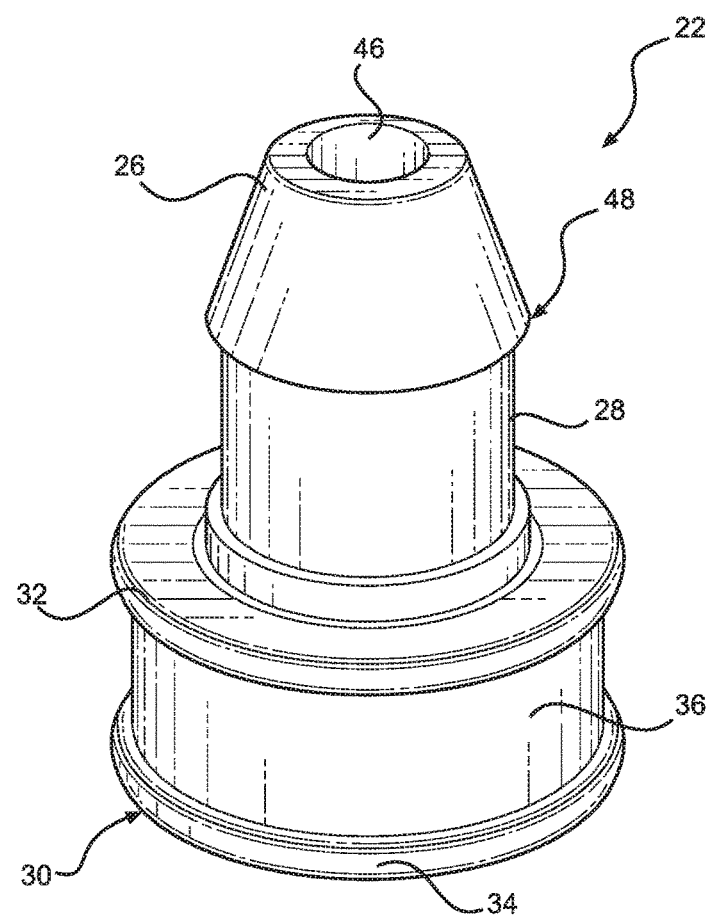
FIG. 4 is a front perspective view of a removable filter according to an embodiment of the present invention.
Figure 5:
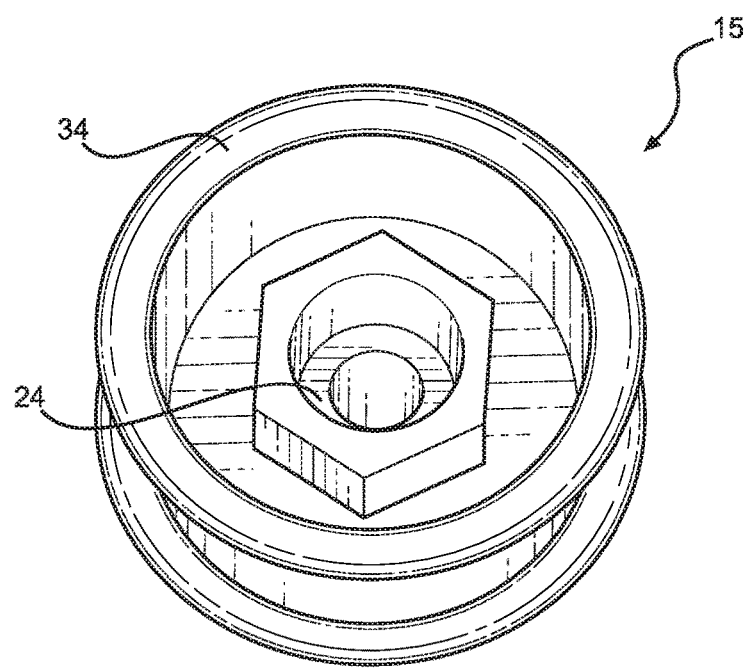
FIG. 5 is an end view of the removable filter of FIG. 4 illustrating a stop and filter medium.

Referring to FIGS. 4 and 5, preferred embodiments of the earplug also include a removable filter 22 that may be inserted into the internal channel 20 of the ear insert. The removable filter 22 has a filter medium 24 placed into an internal channel 46 within the filter 22. If unimpeded, sound waves could travel through the filter 22 via the channel 46 and into the ear of the user. However, placing a filter medium into that channel attenuates the sound waves. The attenuation characteristics of the earplug may be modified based on the removable filter 22 and, more particularly, the filter medium 24 selected. Different filter media can be used to attenuate different types of sounds or different levels of sound. For example, a first filter medium type might be suitable for filtering low and high decibel levels at several frequencies. This type of attenuation might be beneficial where the maximum amount of hearing protection is required. On the other hand, a different filter having a different filter medium may be suitable for only certain decibel levels and certain frequency bands. This type of attenuation may be useful where less than maximum hearing protection is required, such as if certain sounds, like machinery, must be filtered but other sounds, like another person talking or an alarm sounding, should not be filtered.

The filter 22 may be configured for easy customization and use. For example, in certain embodiments, the filter medium 24 may be easily removed and replaced with a different filter medium. In other embodiments, the entire filter 22, including the filter medium 24, may be removed and replaced with an entirely different filter. In some embodiments, the shape or coloring of the filter medium may be varied according to its filtering characteristics. The different colors or shapes used could assist a person in quickly selecting matching filter media for use in multiple earplugs or for selecting specific non-matching filter media to customize an ear plug. The different colors and shapes may also be used to correctly orient the left and right ear plugs. This may be particularly useful when the ear insert 12 is designed specifically for either a person's left ear or their right ear. The body of the filter may be transparent to allow for the type and coloring of the filter medium 24 to be easily identified.

The removable filter 22 includes an insertion tip 48 that may be inserted into the ear insert shown in FIGS. 2 and 3. In particular, the insertion tip 48 has a frustoconical shaped top section 26 that is designed for insertion into the internal channel 20 of the ear insert 12. The sloping walls of the top section 26 facilitate the insertion of the insertion tip 48 into the ear insert 12. With reference to FIGS. 2 and 3, the internal channel 20 of the ear insert 12 is preferably designed such that the opening of the internal channel at the inner portion 12A is smaller in size (D1) than the opening (D2) of the internal channel at the outer portion 12B. The internal channel 20 of the removable filter 22 may have internal sidewalls that constrict smoothly and continuously. Alternatively, the internal channel 20 may have stair stepped internal sidewalls, as shown. The top section 26 of the removable filter 22 is preferably sized so that it can only be inserted into the opening of the internal channel 20 at the outer portion 12B and not the opening at the inner portion 12A of the ear insert 12. This configuration helps to ensure that the removable filter 22 is inserted correctly into the ear insert 12.

Figure 6:
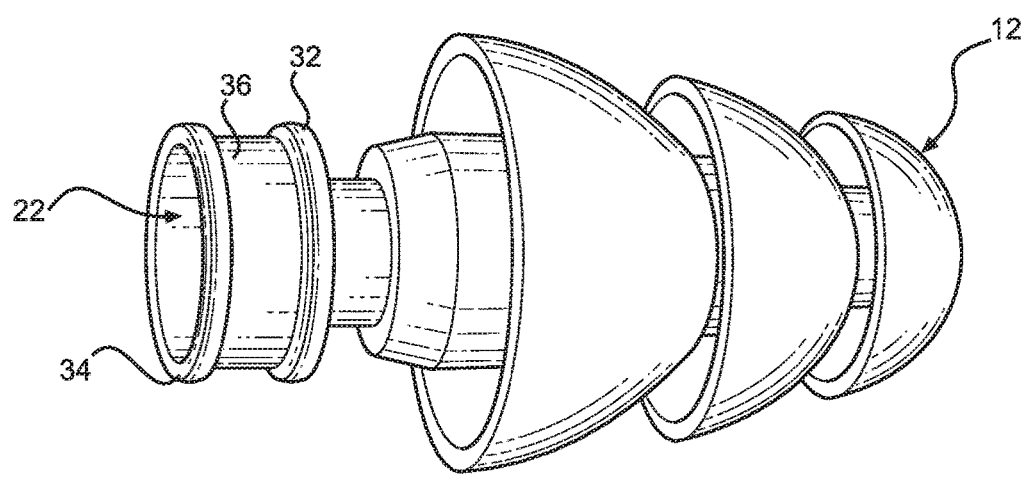
FIG. 6 is an illustration of an insertion tip of a filter partially inserted into an internal channel of an ear insert.
Figure 7:
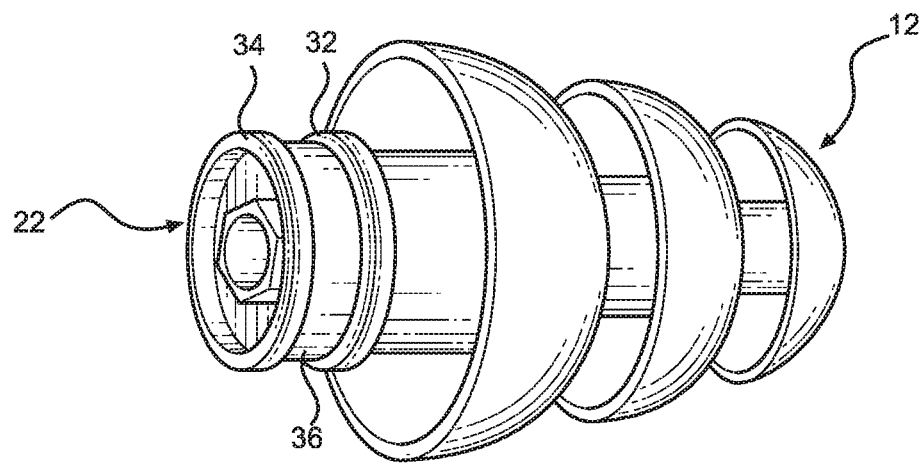
FIG. 7 is an illustration of the ear insert and filter of FIG. 6 after the filter has been fully inserted.

Returning to FIGS. 4 and 5, an extension member 28 connects the sloped top section 26 of the insertion tip 48 to a stop 30. The stop 30 has a much larger diameter than the extension member 28. As such, the insertion tip 48 may be pushed into the ear insert 12 in the manner discussed above until the stop 30 abuts the outer portion 12B of the ear insert. This process is shown in FIGS. 6 and 7. In FIG. 6, a portion of the insertion tip 48 has already been inserted into the ear insert. The deformable body of the ear insert 12 allows the filter to be inserted quite easily while also securely holding the filter in place. As shown in FIG. 7, continuing to push the filter 22 into the ear insert 12 will eventually cause the stop to contact the outer portion 12B of the ear insert.

After the filter 22 has been fully inserted into the ear insert 12 in the manner discussed above, the stop 30 extends away from the outer portion 12B of the ear insert 12. In certain embodiments, the stop 30 is cylindrical in shape and has a first raised ridge 32 located adjacent the extension member 28 of the insertion tip 48. The stop 30 also includes a second raised ridge 34 opposite from the first raised ridge 32. A center section 36 is located between the first and second raised ridges 32, 34 of the cylindrical stop 30. As discussed below, a sound blocking member may be provided with the ear plug for reflecting certain sound waves. The sound blocking member may be securely mounted to the ear plug by being connected to the center section 36 between the first and second raised ridges 32, 34.

Figure 8:
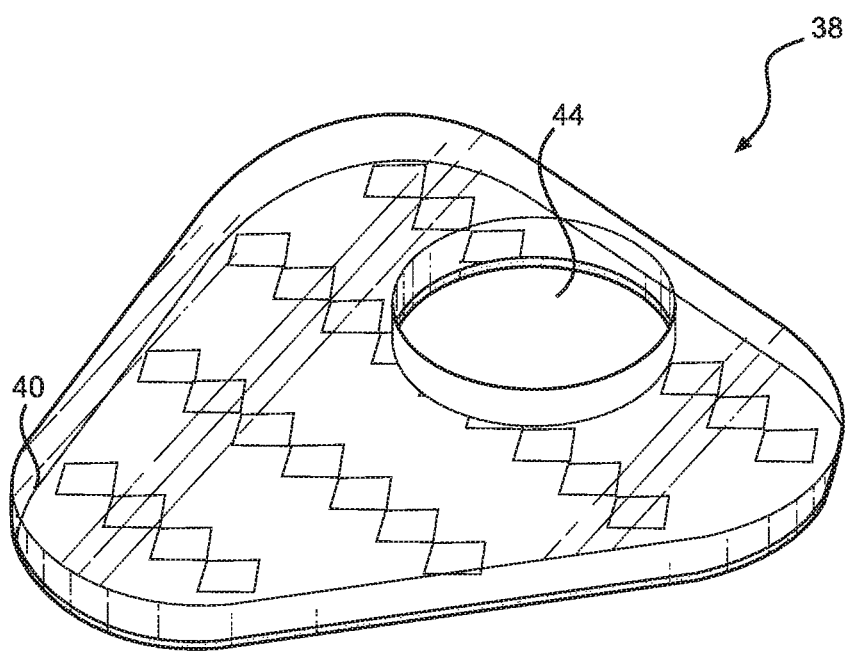
FIG. 8 is a perspective view of a front surface of a sound blocking member according to an embodiment of the present invention.
Figure 9:
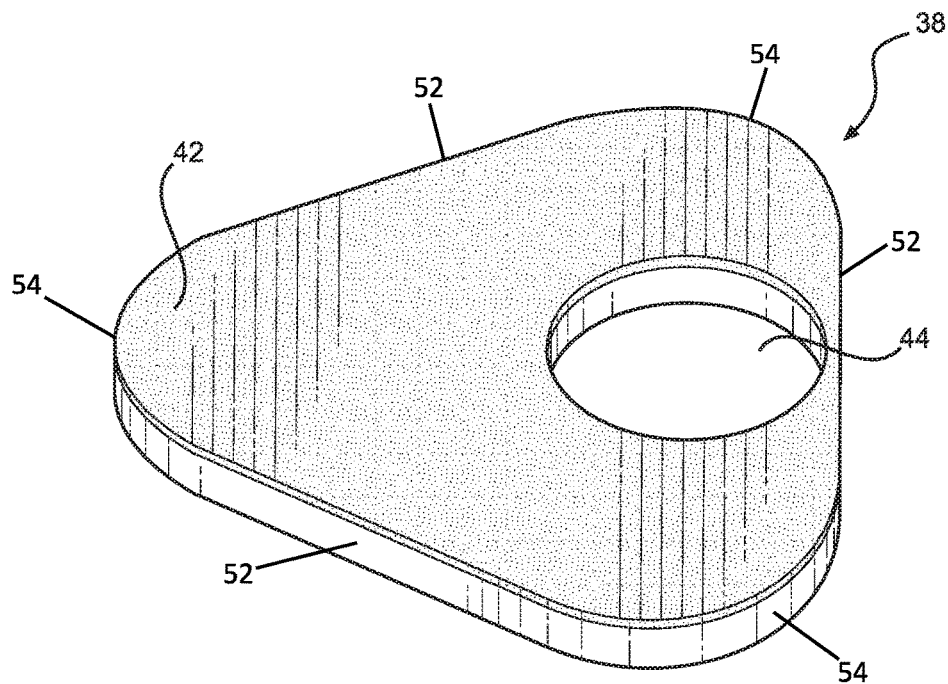
FIG. 9 is a perspective view of a rear surface of the sound blocking member of FIG. 8.
Figure 11:
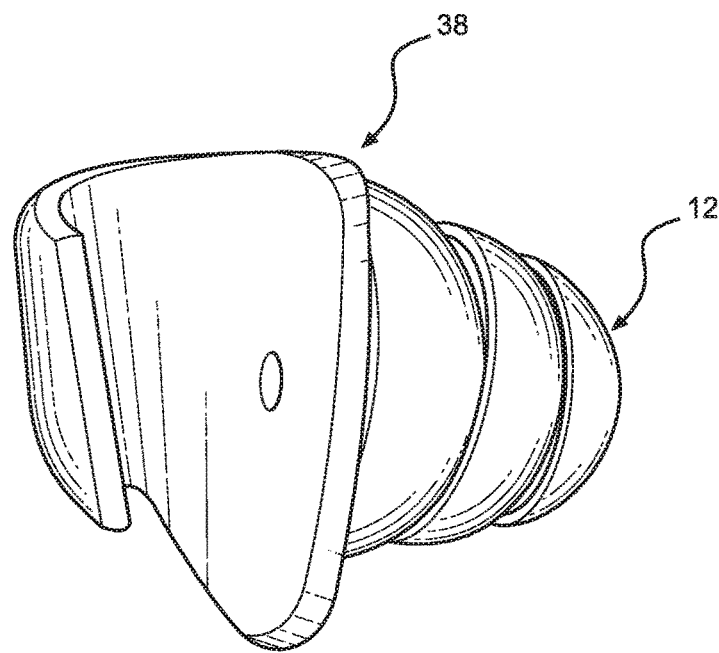
FIGS. 11 and 12 are perspective views of alternative embodiments of earplugs having contoured sound blocking members.
Figure 12:
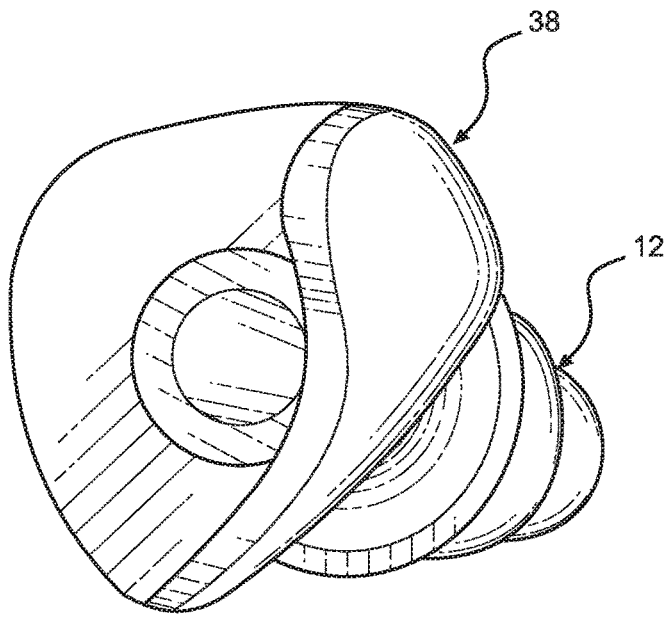

Turning to FIGS. 8 and 9, a sound blocking member 38 is designed to reflect soundwaves away from the user's ear. In certain embodiments, the sound blocking member 38 may also attenuate and reflect sound waves. In other embodiments, a sound blocking member that only attenuates sound may be used in place of a sound reflecting member. For example, the sound blocking member may comprise a sound absorbent material for absorbing sound waves. The sound blocking member 38 works in conjunction with the removable filter 22 discussed above in order to attenuate sounds that the user hears. The sound blocking member 38 is secured between the first and second raised ridges 32,36 of the stop 30 and covers the concha of the user's ear in order to block sounds from entering the ear. The sound blocking member 38 may cover only a portion of the concha or may cover the entire concha. In certain embodiments, the sound blocking member 38 may be customized to precisely fit the ear of the user. In other embodiments, the sound blocking member 38 is round, oval or polygonal in shape. In certain embodiments, the sound blocking member 38 is plate-like and has a planar front surface 40 and planar back surface 42. In other embodiments, as shown in FIGS. 11 and 12, the sound blocking member 38 is contoured and may have projections, including ridges or lips that extend away from the front surface 40. In other embodiments, the sound blocking member may not reflect or absorb sound at all but may merely be used as a decorative faceplate containing an ornamental design that is customizable to the user's liking.

An ornamental design may be provided on the sound blocking member 38 in order to improve the aesthetics of the earplug 10. This ornamental design may be applied on the front surface, 40 back surface, 42 or both. If applied on the back surface 42, the material used for the sound blocking member 38 should be at least partially transparent so that the design can be seen while looking at the front surface 40. In other embodiments, the ornamental design may be formed into the material of the sound blocking member 38. The ornamental design may be applied in a variety of ways, including by a surface application such as painting or surface texturing. On the other hand, the design may be applied to a separate substrate and then affixed to the front or back surfaces 40, 42. The ornamental design is preferably interchangeable or removable so that different designs may be used. For example, a substrate having a design printed thereon may be adhered to the surface. To change the ornamental design, the substrate may be removed and replaced or a new substrate may be placed over the old substrate. In other embodiments, multiple interchangeable sound blocking members may be provided, each with a different ornamental design. Preferably, a protective coating, such as a resin top coat, is applied over the ornamental design to protect it against damage.

Figure 10:
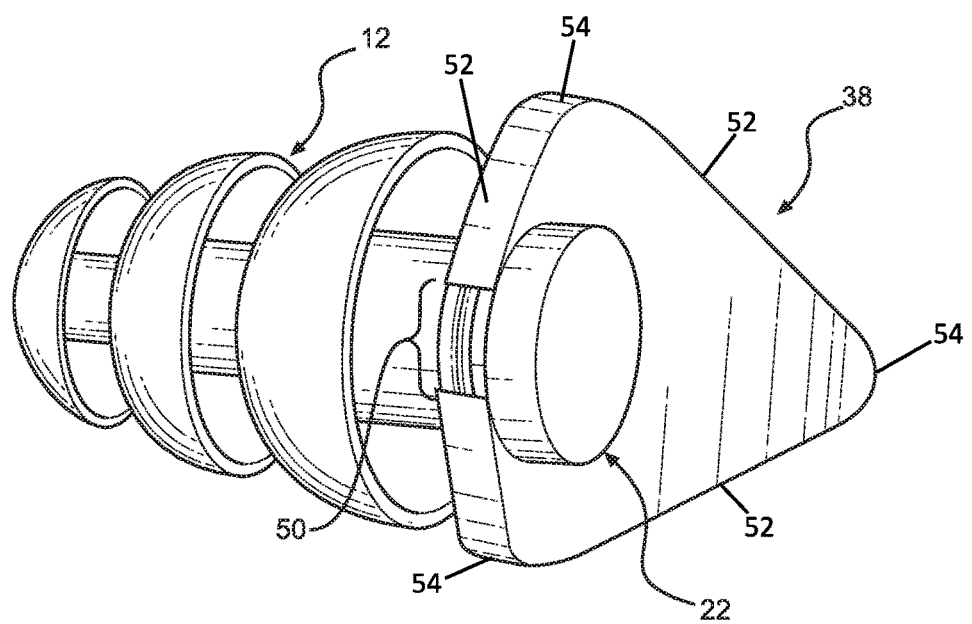
FIG. 10 is a perspective view of an alternative embodiment of an earplug having a sound blocking member with an opening located along an outer edge.

As shown in FIGS. 9 and 10, one embodiment of the sound blocking member 38 is generally triangular, having three sides 52 and three rounded vertices 54. In this embodiment, the central opening 44 of the sound blocking member 38 is preferably disposed adjacent one of the three sides 52.

The sound blocking member 38 may be mounted to the ear insert 12 in a variety of ways. In one embodiment, the sound blocking member 38 and the removable filter 22 may be integrally formed as a single unit. In another embodiment, the sound blocking member 38 may be removably mounted to the removable filter 22. The sound blocking member 38 may include an opening 44. The opening 44 is sized so that it may slide over the first raised ridge 32 of the cylindrical stop 30 and be retained in the center section 36 between the first and second raised ridges 32, 34. The opening 44 is positioned so that the sound blocking member 38 extends across at least a portion of the concha once the earplug 10 has been properly assembled and inserted into a user's ear. In the embodiment shown, the sound blocking member 38 surrounds the entire opening 44. In other embodiments, as shown in FIG. 10, the opening 44 may be formed at an edge of the sound blocking member 38 such that a slot 50 is created. The slot 50 is sized and configured to slide around the center section 36 of the stop 30 (shown in FIG. 4).

In certain embodiments, an earplug kit is provided for selectively attenuating and blocking sound waves directed toward an ear canal of a user. The kit includes an ear insert and a sound blocking member that are similar to those described above. The kit also includes a plurality of interchangeable filters that may each be removably inserted into an internal channel of the ear insert. The filters have different filter media installed in them to provide different filtering characteristics, including the type and level of sounds that are filtered. In some embodiments, the kit may also include multiple interchangeable sound blocking members. These interchangeable sound blocking members may have different ornamental designs so that the style of the earplug can be easily and quickly altered. Additionally, the interchangeable sound blocking members may have different shapes or sizes or be made from different materials to vary the aesthetics as well their sound reflective or absorptive properties.

The foregoing description of preferred embodiments for this disclosure has been presented for purposes of illustration and description. It is not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated.

What is claimed is:
1. An earplug for use in an ear comprising:
    an ear insert having an inner portion and an outer portion, the inner portion sized and configured for insertion into an ear canal to attenuate sound waves directed toward the ear canal, and the outer portion configured to be disposed outside the ear canal, the ear insert comprising a flexible body having an elongate shape with an internal channel extending therethrough;
    a plurality of interchangeable sound attenuation filters comprising:
        a first sound attenuation filter operable to be disposed inside the internal channel of the ear insert, the first sound attenuation filter having a first filter medium for attenuating sound waves passing into the ear canal at low and high decibel levels to provide a maximum amount of hearing protection across multiple frequencies; and
        a second sound attenuation filter operable to be disposed inside the internal channel of the ear insert when the first sound attenuation filter is removed there from, the second sound attenuation filter having a second filter medium for attenuating sound waves passing into the ear canal at one or more certain select decibel levels to provide less than a maximum amount of hearing protection at one or more certain select frequencies; and a sound blocking member attached to and extending outwardly from the outer portion of the ear insert to cover at least a portion of a concha of the ear, the sound blocking member for reflecting or absorbing at least a portion of sound waves directed toward the ear canal.

2. The earplug of claim 1 wherein the flexible body comprises at least one conformable vane projecting from an external surface of the flexible body configured to work cooperatively with the flexible body to conform to a portion of the ear canal when the inner portion of the ear plug is inserted into the ear.

3. The earplug of claim 1 wherein the first and second sound attenuation filters each comprises an insertion tip configured for insertion into the internal channel of the ear insert, a stop configured to abut the outer portion of the ear insert, and an internal channel extending through the filter through which filtered sound waves pass.

4. The earplug of claim 3 wherein the sound blocking member has a central opening that engages the stops of the first and second sound attenuation filters, is symmetrical in shape in at least one dimension relative to the central opening, and extends outwardly from the stop to cover a portion of a concha of the ear.

5. The earplug of claim 3 wherein the stop is cylindrical in shape and has:
　a first raised ridge located adjacent to the insertion tip and abutting the outer portion of the ear insert;
　a second raised ridge disposed opposite from the first raised ridge; and
　a center section located between the first and second raised ridges of the cylindrical stop,
　wherein the sound blocking member includes an opening configured to slide over the second raised ridge of the stop and to be retained in the center section by the first and second raised ridges, whereby the sound blocking member is removably connected to the ear insert.

6. The earplug of claim 1 wherein the internal channel of the ear insert has a first diameter at the inner portion and has a second diameter at the outer portion, wherein the first and second sound attenuation filters are configured to removably engage the internal channel at the outer portion but not at the inner portion of the ear insert.

7. The earplug of claim 1 wherein the sound blocking member comprises a substantially flat plate.

8. The earplug of claim 1 wherein the sound blocking member comprises a plate that is at least partially transparent and further comprises a surface layer disposed on a first side of the plate that is visible through a second side of the plate.

9. The earplug of claim 1 wherein the ear insert comprises a conformable foam ear insert configured to conform to a portion of the ear canal when an end of the foam ear insert is inserted into the ear.

10. An earplug kit for selectively attenuating and blocking sound waves directed toward an ear canal of an ear, the kit comprising:
　an ear insert comprising:
　　a flexible body defining an elongate shape having an inner portion sized and configured for insertion into an ear canal, and an outer portion, the flexible body configured to conform to a portion of the ear canal when the inner portion of the ear plug is inserted into the ear canal; and
　　an internal channel extending through the flexible body;
　a sound blocking member disposed adjacent the outer portion of the ear insert, the sound blocking member for reflecting or absorbing at least a portion of sound waves directed toward the ear canal; and
　a plurality of interchangeable sound attenuation filters configured for removable insertion into the internal channel of the ear insert, each interchangeable sound attenuation filter having a filter medium for attenuating sound waves passing into the ear canal according to fixed attenuation characteristics that are different from fixed attenuation characteristics of filter media of other of the interchangeable sound attenuation filters.

11. The earplug kit of claim 10 wherein each of the plurality of interchangeable sound attenuation filters comprises an insertion tip configured for insertion into the internal channel at the outer portion of the ear insert, a stop configured to abut the outer portion of the ear insert, and an internal channel extending through the filter configured to permit sound waves to pass through the filter, wherein the filter medium is disposed inside the internal channel of the filter.

12. The earplug kit of claim 11 wherein the sound blocking member comprises an opening, and wherein the stop of each of the plurality of filters comprises a first raised ridge located adjacent the insertion tip, a second raised ridge, and a center section located between the first and second raised ridges of the stop, and wherein the opening of the sound blocking member is configured to slide over at least one of the raised ridges of the stop and to be retained in the center section by the raised ridges, whereby the sound blocking member is removably connected to the ear insert.

13. The earplug kit of claim 10 further comprising multiple interchangeable sound blocking members having unique ornamental designs disposed thereon, wherein each of the sound blocking members may be completely removed and replaced with another of the sound blocking members.

14. The earplug kit of claim 10 wherein each of the plurality of interchangeable sound attenuation filters has different fixed attenuation characteristics for attenuating different levels or frequencies of sound, wherein the fixed attenuation characteristics are based at least in part on the filter media located in each of the plurality of filters.

15. An ear plug for use in an ear, the ear plug comprising:
　an ear insert having an inner portion and an outer portion, the inner portion sized and configured for insertion into an ear canal to attenuate sound waves directed toward the ear canal, and the outer portion configured to be disposed outside the ear canal; and
　an interchangeable faceplate configured for removable attachment to the outer portion of the ear insert, the interchangeable faceplate operable to cover a portion of a concha of the ear when the faceplate is attached to the outer portion of the ear insert, wherein the portion of the concha of the ear is uncovered when the interchangeable faceplate is detached from the outer portion of the ear insert, the faceplate having a front surface, a back surface, and an ornamental design disposed on one or both of the front and back surfaces that is visible when looking at the front surface.

16. The ear plug of claim 15 further comprising a removable filter having:
　an insertion tip configured for removable insertion into an internal channel of the ear insert;
　a stop configured to abut the outer portion of the ear insert when the insertion tip has been inserted into the internal channel of the ear insert via an opening located at the outer portion of the ear insert;

an internal channel extending through the filter through which filtered sound waves pass; and a filter medium for attenuating sound waves passing through the filter disposed in the internal channel of the filter, wherein the interchangeable faceplate is configured to removably attach to a portion of the stop of the filter.

17. The ear plug of claim 16 further comprising:

a first raised ridge formed on the stop and located adjacent the insertion tip that abuts the outer portion of the ear insert when the insertion tip has been inserted into the internal channel of the ear insert via the opening located at the outer portion of the ear insert;

a second raised ridge formed on the stop;

a center section located on the stop between the first and second raised ridges; and an opening formed into the faceplate that is configured to engage the center section of the stop and to be retained in the center section by the ridges.

18. The earplug of claim 1 wherein the sound blocking member comprises a triangular shape having three sides and three rounded vertices, the sound blocking member having a central opening that receives the outer portion of the ear insert, wherein the central opening is disposed adjacent one of the three sides of the sound blocking member.

19. The earplug of claim 18 wherein the central opening intersects one of the three sides of the sound blocking member, thereby forming a slot through which the outer portion of the ear insert is received into the central opening.

20. The earplug of claim 1 wherein a central longitudinal axis of the filter media is collinear with a central longitudinal axis of the internal channel of the ear insert.

21. An earplug for use in an ear comprising:

an ear insert having an inner portion and an outer portion, the inner portion configured to be inserted into an ear canal to attenuate sound waves, and the outer portion configured to be disposed outside the ear canal, the ear insert comprising a flexible body having an elongate shape with an internal channel extending therethrough;

a removable and replaceable sound attenuation filter disposed within the internal channel of the ear insert, the sound attenuation filter comprising a filter medium for attenuating sound waves passing into the ear canal according to attenuation characteristics that may be modified based on selection of the filter medium to achieve a selected level of hearing protection; and a generally triangular sound blocking member attached to and extending outwardly from the outer portion of the ear insert to cover at least a portion of a concha of the ear, the sound blocking member configured to reflect or absorb at least a portion of sound waves directed toward the ear canal, the sound blocking member comprising:

a front surface;

a back surface;

three sides;

three rounded vertices; and a central opening disposed adjacent one of the three sides, the central opening sized and configured to receive the outer portion of the ear insert.

\* \* \* \* \*